United States Patent
Oakes

(10) Patent No.: US 11,273,257 B2
(45) Date of Patent: Mar. 15, 2022

(54) INFUSION PUMP SYSTEM

(71) Applicant: ViCentra B.V., Utrecht (NL)

(72) Inventor: Tim Oakes, Swansea (GB)

(73) Assignee: ViCentra B.V., Utrecht (NL)

( * ) Notice: Subject to any disclaimer, the term of this patent is extended or adjusted under 35 U.S.C. 154(b) by 228 days.

(21) Appl. No.: 16/068,304

(22) PCT Filed: Dec. 12, 2016

(86) PCT No.: PCT/EP2016/080681
§ 371 (c)(1),
(2) Date: Jul. 5, 2018

(87) PCT Pub. No.: WO2017/118535
PCT Pub. Date: Jul. 13, 2017

(65) Prior Publication Data
US 2019/0009022 A1    Jan. 10, 2019

(30) Foreign Application Priority Data

Jan. 6, 2016 (GB) ..................... 1600235

(51) Int. Cl.
*A61M 5/168* (2006.01)
*A61M 5/142* (2006.01)

(52) U.S. Cl.
CPC .... *A61M 5/16831* (2013.01); *A61M 5/14224* (2013.01); *A61M 5/14244* (2013.01);
(Continued)

(58) Field of Classification Search
CPC .. A61M 2230/201; A61M 2005/14268; A61M 2005/16863; A61M 5/16831;
(Continued)

(56) References Cited

U.S. PATENT DOCUMENTS

| | | | |
|---|---|---|---|
| 4,201,085 A | | 5/1980 | Larson |
| 4,244,365 A | * | 1/1981 | McGill ............ A61M 5/16854 340/611 |

(Continued)

FOREIGN PATENT DOCUMENTS

| | | |
|---|---|---|
| CN | 105259423 A | 1/2016 |
| DE | 4021473 A1 | 1/1992 |
| GB | 2125553 A | 3/1984 |

OTHER PUBLICATIONS

International Search Report and Written Opinion for International Application No. PCT/EP2016/080681, dated Feb. 21, 2017, 9 pages.

(Continued)

*Primary Examiner* — Amber R Stiles
(74) *Attorney, Agent, or Firm* — Armstrong Teasdale LLP

(57) ABSTRACT

Infusion pump system and associated methods The invention provides a fluid delivery system (1), comprising: an outlet tube (6); a pump (2) for pumping liquid along a fluid path (100) including the outlet tube; a closed sensing tube (104) branched from the fluid path which, in use, is filled with gas; and a sensor (108) configured to sense movement of a liquid front within the sensing tube and, responsive to sensing of said movement, determine that a partial or total occlusion has occurred within the outlet tube.

18 Claims, 10 Drawing Sheets

(52) U.S. Cl.
CPC .... *A61M 5/16813* (2013.01); *A61M 5/16854* (2013.01); *A61M 2005/14268* (2013.01); *A61M 2005/16863* (2013.01); *A61M 2205/123* (2013.01); *A61M 2205/3306* (2013.01); *A61M 2205/3317* (2013.01); *A61M 2205/3584* (2013.01); *A61M 2205/502* (2013.01); *A61M 2230/201* (2013.01)

(58) Field of Classification Search
CPC .......... A61M 5/14244; A61M 5/14224; A61M 5/16854; A61M 5/16813; A61M 2205/3306; A61M 2205/3317; A61M 2205/3584; A61M 2205/502; A61M 2205/123; A61M 2205/3382; A61M 2205/3355; A61M 2205/3351
See application file for complete search history.

(56) References Cited

U.S. PATENT DOCUMENTS

| | | |
|---|---|---|
| 4,395,259 A | 7/1983 | Prestele |
| 5,853,386 A | 12/1998 | Davis |
| 6,575,026 B1 | 6/2003 | Debar |
| 6,830,558 B2 * | 12/2004 | Flaherty ............ A61M 5/14248 604/31 |
| 7,892,199 B2 * | 2/2011 | Mhatre ............. A61M 5/14566 604/65 |
| 8,486,005 B2 * | 7/2013 | Yodfat ............. A61M 5/16831 604/67 |
| 2002/0186140 A1 | 12/2002 | Anderson |
| 2008/0188810 A1 * | 8/2008 | Larsen ............. A61M 5/14248 604/152 |
| 2009/0093786 A1 * | 4/2009 | Renaux ............ A61M 5/16854 604/500 |
| 2011/0118662 A1 * | 5/2011 | Mhatre ............. A61M 5/14248 604/67 |
| 2011/0172594 A1 | 7/2011 | Yodfat et al. |
| 2011/0294640 A1 * | 12/2011 | Dolecek .................. B04B 15/00 494/1 |
| 2013/0060194 A1 * | 3/2013 | Rotstein ............. A61M 39/284 604/151 |
| 2014/0276550 A1 * | 9/2014 | Uram ................ A61M 5/16877 604/503 |
| 2015/0308877 A1 | 10/2015 | Faraldi |

OTHER PUBLICATIONS

First Office Action, Chinese Patent Application No. 201680078009. 1, 22 pages, dated Apr. 29, 2020.

* cited by examiner

INFUSION PUMP SYSTEM

CROSS-REFERENCE TO RELATED APPLICATIONS

This application is the national stage entry of PCT/EP2016/080681, filed on Dec. 12, 2016, which claims priority to British Patent Application No. 1600235.4, filed Jan. 6, 2016, which are incorporated by reference in their entirety herein.

TECHNICAL FIELD

The present invention relates to an infusion pump system, for example for delivery of a liquid therapeutic product, and associated methods and a computer-readable medium comprising instructions for carrying out those methods.

BACKGROUND

Infusion systems for the infusion of liquid therapeutic products into the human or animal body are known in the art, e.g. from U.S. Pat. No. 4,395,259. Such systems are particularly, though not exclusively, intended for the infusion of insulin into the body for diabetes therapy. The system has an infusion device which may be implanted or worn externally on the body, and a remote controller that can wirelessly monitor the function of the infusion device. The infusion device includes a pump, a reservoir of the therapeutic product, control electronics and a battery power supply.

Such devices tend to be relatively large in size and have a high electrical power requirement necessitating frequent replacement or recharging of the battery. Extended or frequent periods where a user cannot receive delivery of the therapeutic product due to refilling or replacement of the reservoir of therapeutic product, or replacement or recharging of the battery are undesirable from a medical standpoint and are inconvenient for the user.

Moreover, the wetted parts of the infusion device in contact with the liquid therapeutic product require periodic flushing or replacement. Whilst disposable reservoirs are known, their interface with the pump part of the infusion device tends to result in a complex, costly solution having a high electrical power requirement to achieve the accuracy required for the delivery of medication at flow rate increments in the region of 25 to 50 nano litres per hour. More recently disposable, or semi disposable pump designs have become available but minimising the cost of any disposable parts of the device still presents a significant barrier.

SUMMARY OF INVENTION

According to a first aspect of the present invention, there is provided a fluid delivery system, comprising: an outlet tube; a pump for pumping liquid along a fluid path including the outlet tube; a closed sensing tube branched from the fluid path which, in use, is filled with gas; and a sensor configured to sense movement of a liquid front within the sensing tube and, responsive to sensing of said movement, determine that a partial or total occlusion has occurred within the outlet tube.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

Figure 1:
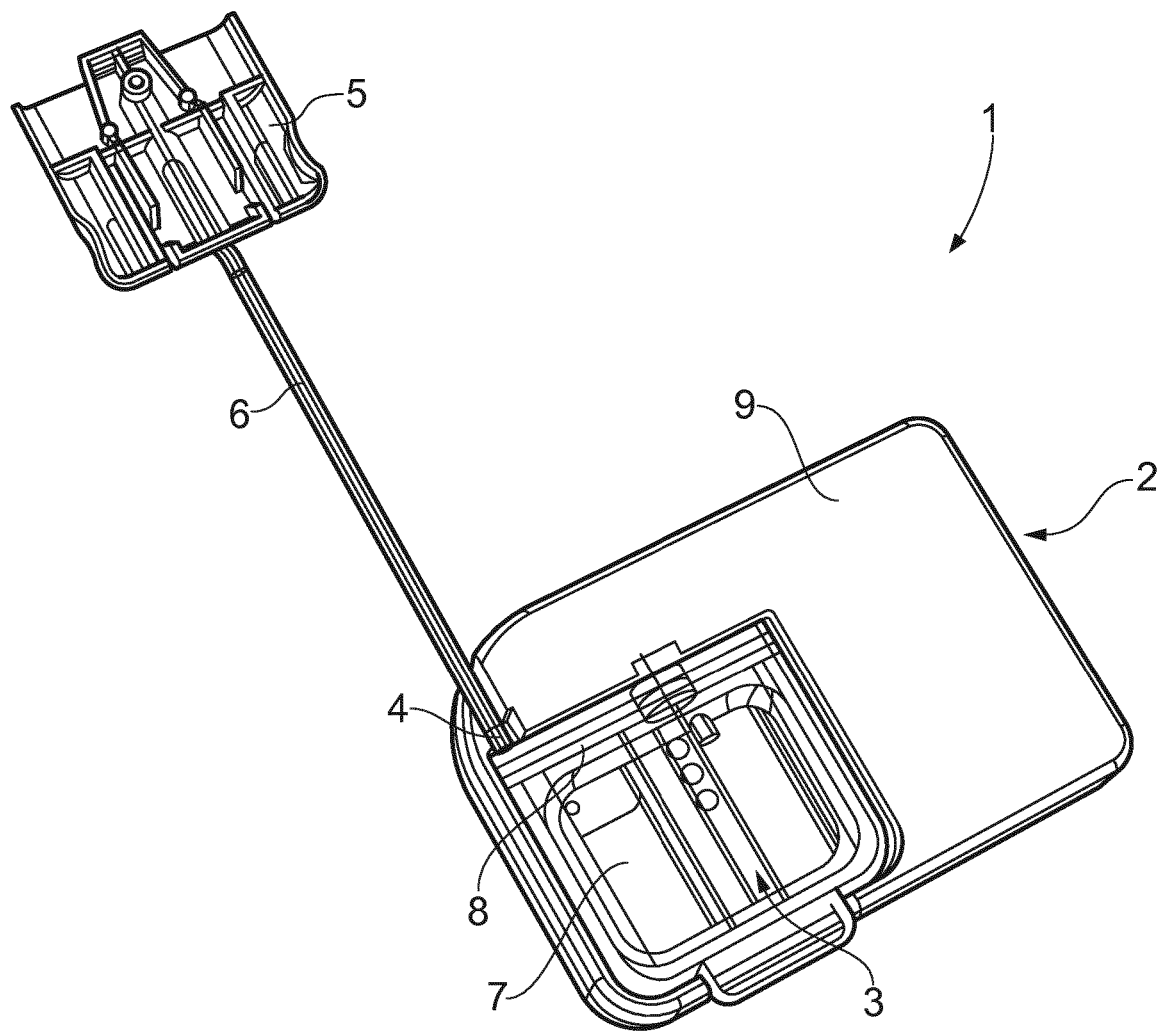
FIG. 1 illustrates a wearable part of an external infusion system.

FIG. 1 shows the wearable part of an external infusion system 1 for the continuous subcutaneous infusion of insulin into the human body through repetitive small pulses of infusion. The infusion system 1 comprises a pump part 2, a cartridge 3 having an outlet port 4 connected to an infusion set 5 via an infusion tube 6.

The infusion set 5 includes a subcutaneous cannula and an adhesive mount for adhering the infusion set to the patient's skin. The cannula is typically made of flexible plastic so as not to cause discomfort for the patient during use. The infusion set is typically installed into a spring loaded insertion device together with a steel needle surrounding the cannula. Upon insertion, the steel needle is removed leaving the cannula in place. Alternative infusion sets, which may replace the infusion set shown in FIG. 1, comprise a steel needle instead of the cannula.

Depending on the desired positioning of the pump part 2 with respect to the infusion set 5 during use the length of the infusion tube 6 may be longer or shorter than that shown in FIG. 1, and indeed the infusion set 5 may be coupled directly to the output port 4 of the pump where close coupling of the infusion set 5 and the pump part 2 is desired, thereby avoiding the need for the flexible infusion tube 6.

The cartridge 3 includes a reservoir 7 for storing a supply of insulin and a pumping chamber 8. The pump part 2 contains an actuator, a rechargeable battery power supply and control electronics for controlling the actuator.

The cartridge 3 is removably attachable to a housing 9 of the pump part 2 such that when the cartridge 3 is attached to the housing 9 a drive member of the actuator is operatively coupled to the pumping chamber 8 for delivering a supply of insulin from the reservoir 7 to the outlet port 4 and into the infusion set 5 via the infusion tube 6.

Figure 2:
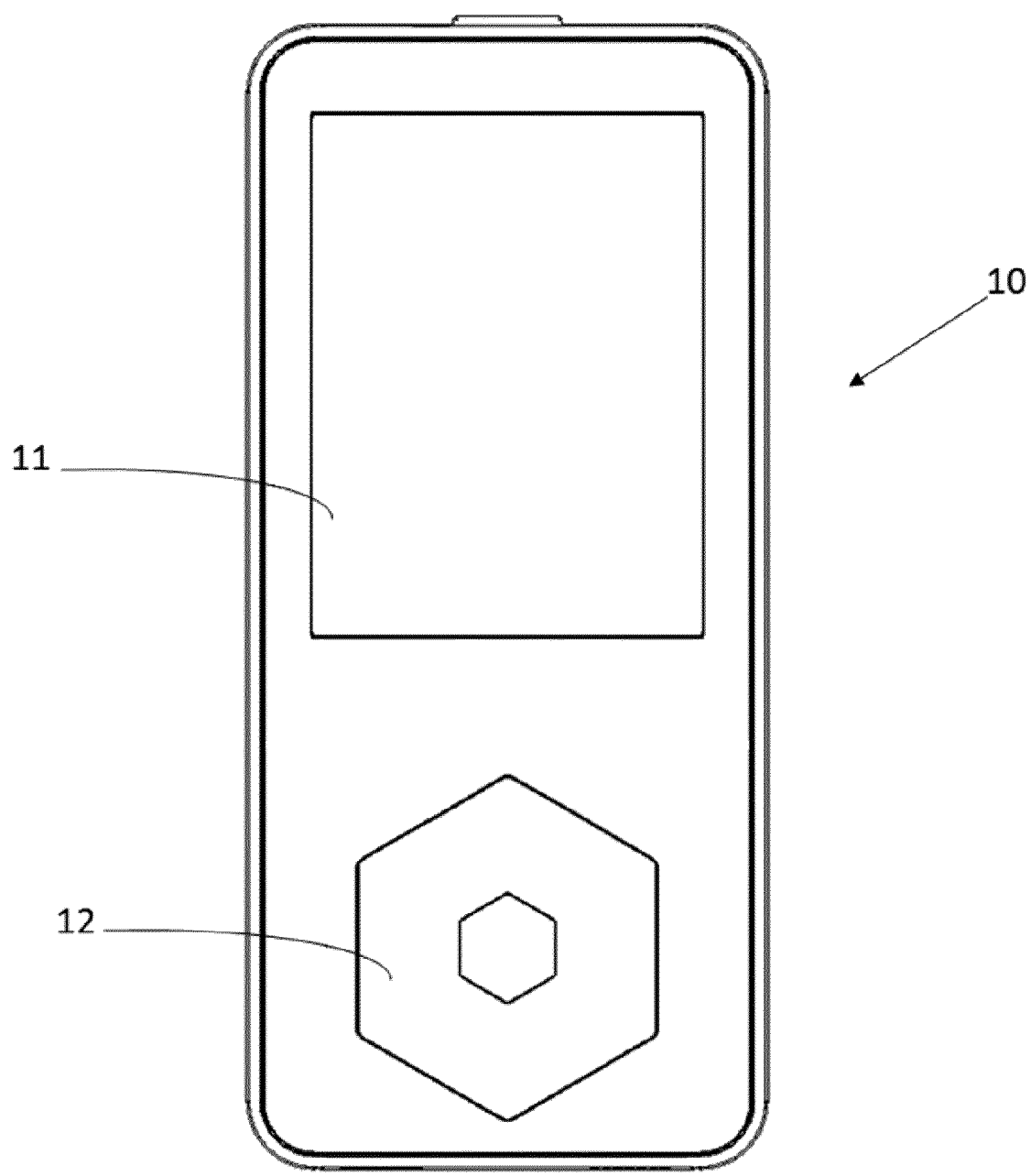
FIG. 2 illustrates a handset of the infusion system for wireless communication with the wearable part.

The control electronics of the pump part 2 includes a transceiver for wireless communication with a user control handset 10 shown in FIG. 2. The handset 10 also includes a transceiver for wireless communication with the pump part 2. The wireless communication may be via Bluetooth™ or other radio frequency near field communication means. The handset 10 includes a graphical user interface 11 and a tactile user interface 12. The handset 10 enables a user to perform the following functions:

Define and store basal profiles;

Transfer an active basal profile to the pump 2;

Define and transmit a bolus request to the pump 2;

Define and transmit a temporary basal to the pump 2;

View a graphical recommendation of a bolus based on glucose readings from a separate blood glucose meter or entered manually following a blood glucose meter reading from a separate blood glucose meter (not shown);

View graphically pump performance over time;

Request the current status of the pump 2 (including what insulin delivery is currently in progress, battery status, alarm conditions, insulin reservoir level, etc.).

The handset 10 is also enabled for internet connectivity, e.g. by a wireless radio connection such as Bluetooth™ or Wi-Fi between the handset and remote internet connected devices. The internet connectivity enables two-way patient support either directly or via an intermediate internet connected device such as a PC, laptop or mobile device.

Figure 3:
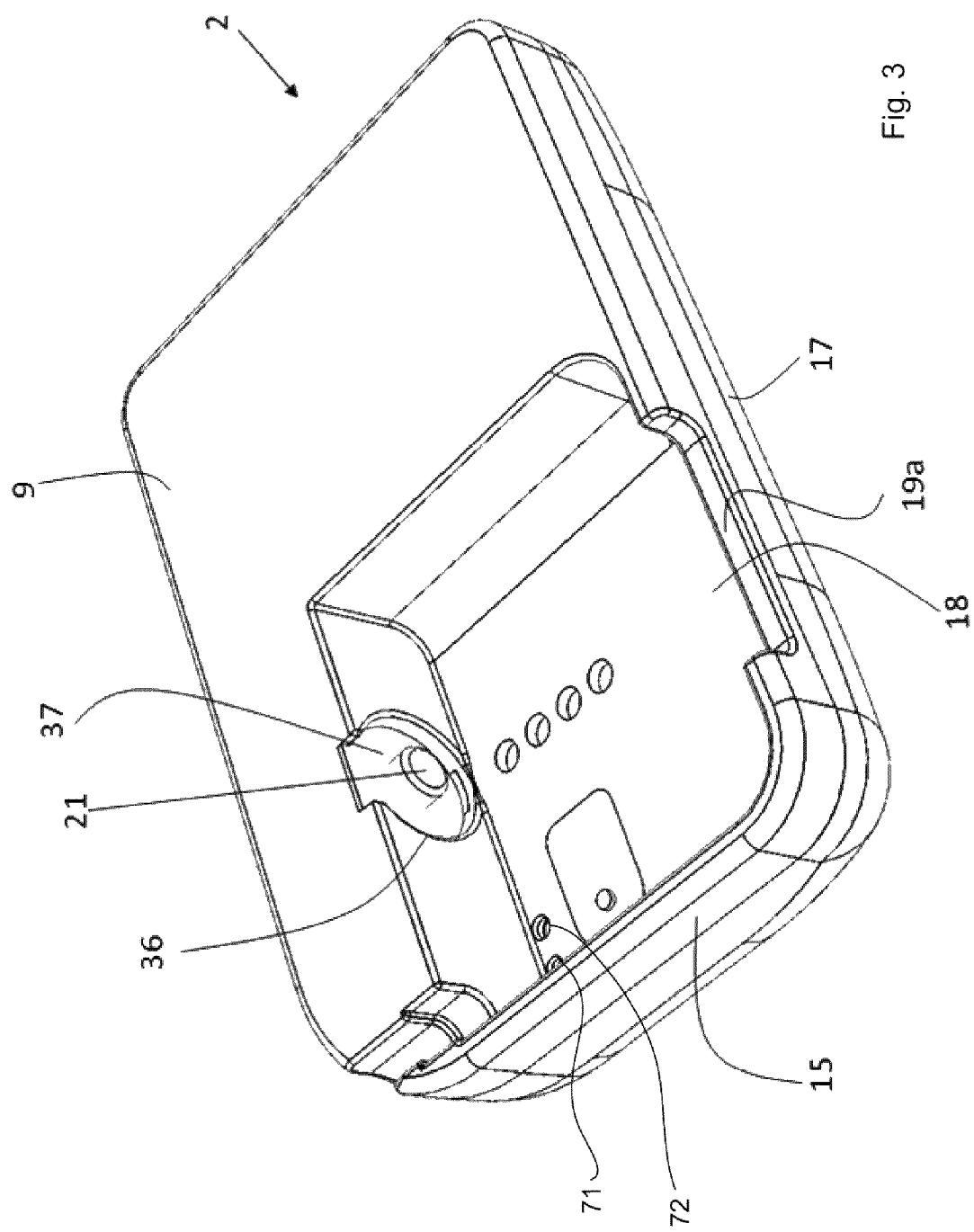
FIG. 3 illustrates a durable pump part of the infusion system.
Figure 4:
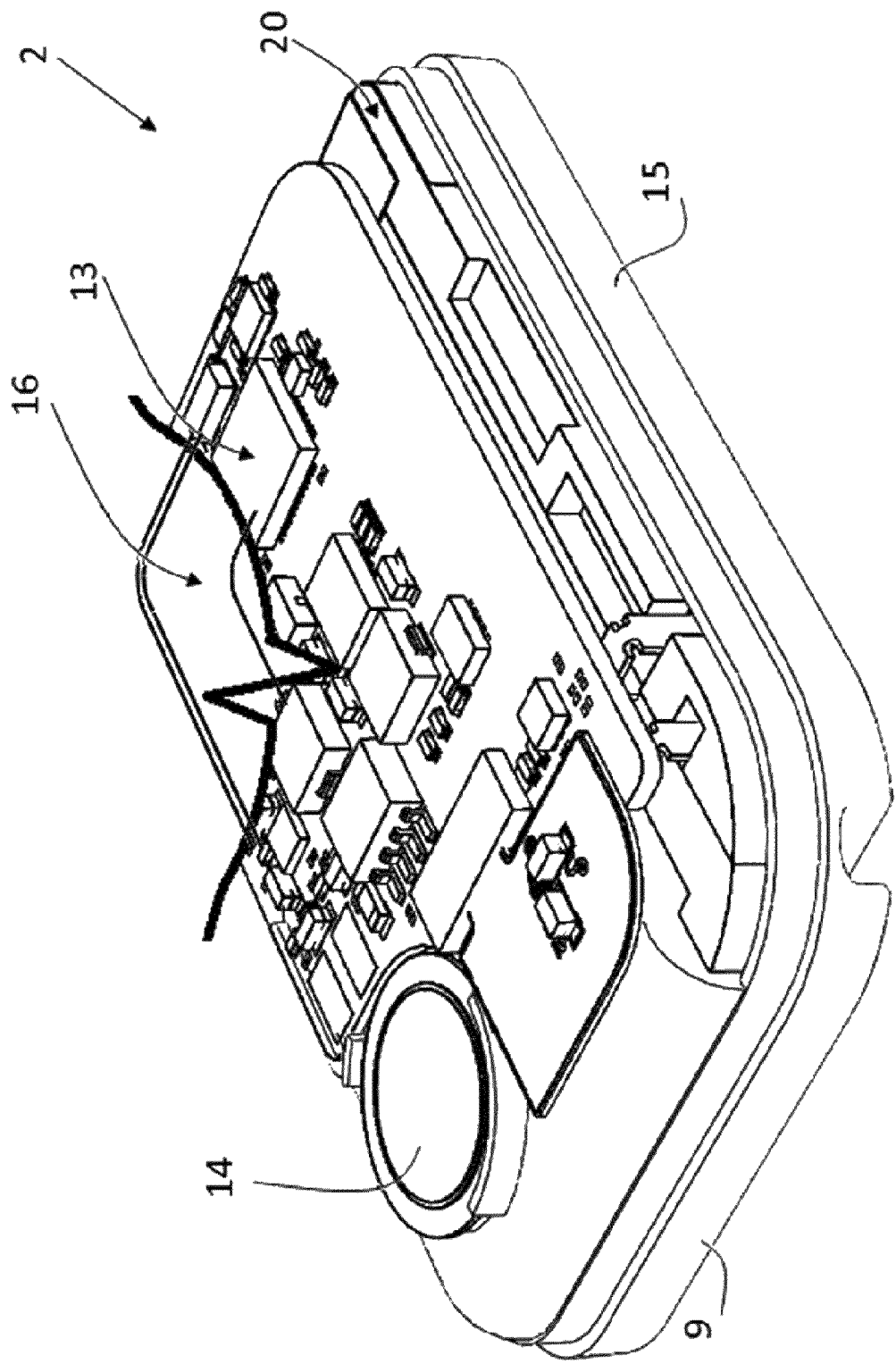
FIG. 4 illustrates the durable pump part with its cover removed.

Turning next to FIGS. 3 and 4, the pump part 2 will now be described in detail. As shown in FIGS. 3 and 4 the pump part 2 includes an actuator 20 for driving a drive member 21 in reciprocating motion. The housing 9 also contains a printed circuit board 13 carrying the control electronics, a piezo-electric sounder 14, a chassis 15 for supporting the actuator 20, the PCB 13, the piezo-electric sounder 14 and defining a battery holder 16 for receiving a rechargeable battery (not shown). In FIG. 4 a top cover 17 (visible in FIG. 3) has been removed for clarity. As best shown in FIG. 3, the chassis 15 defines a recess 18 for receiving the cartridge 3. In FIG. 3 the pump 2 is shown with the cartridge 3 removed. The pump part 2 and the cartridge 3 have cooperating retaining features 19a, 19b for the secure retention and ready removal of the cartridge 3 from the pump part 2 using a snap fit type connection.

Figure 5:
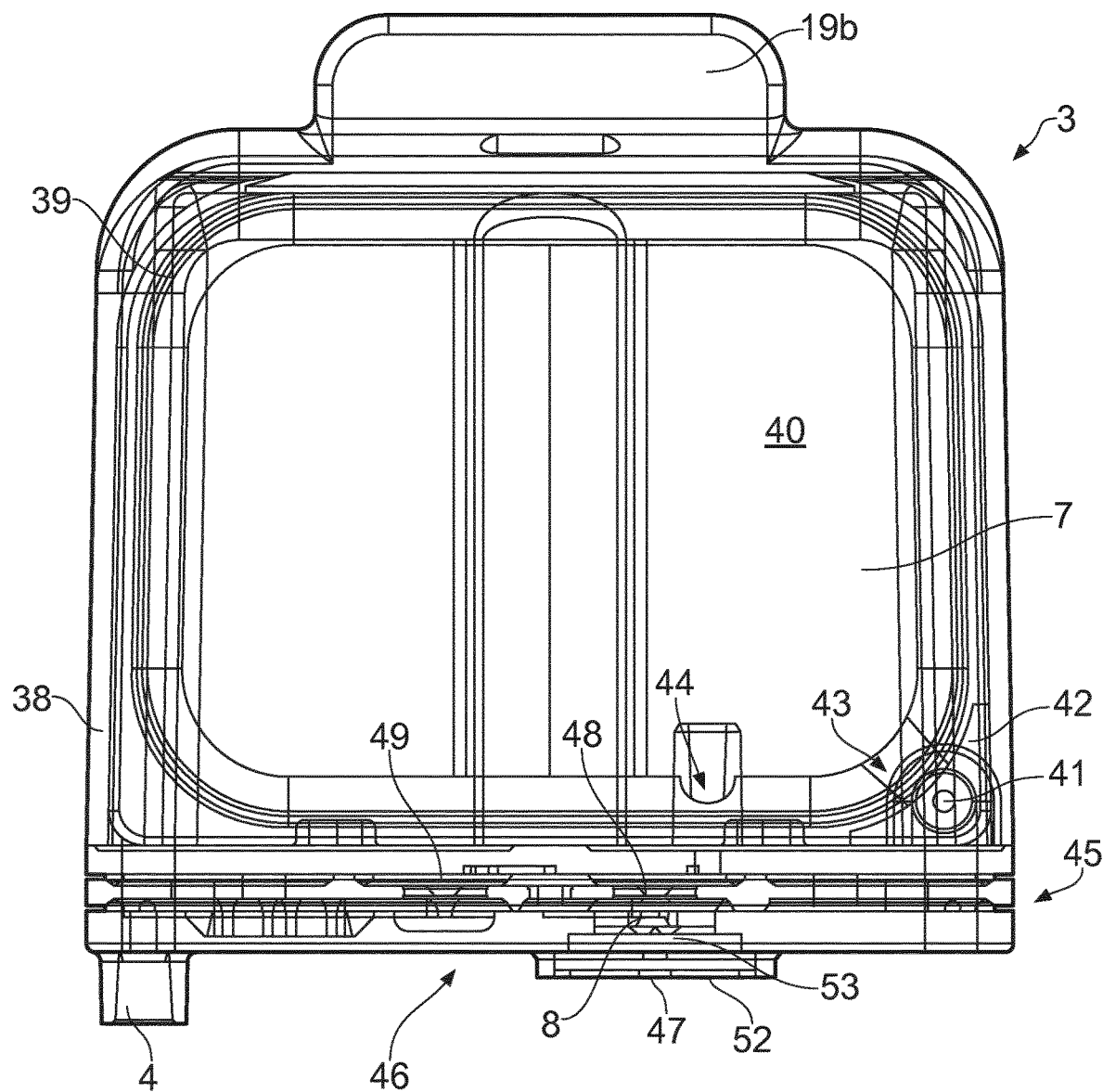
FIG. 5 shows a plan view of the cartridge.
Figure 6:
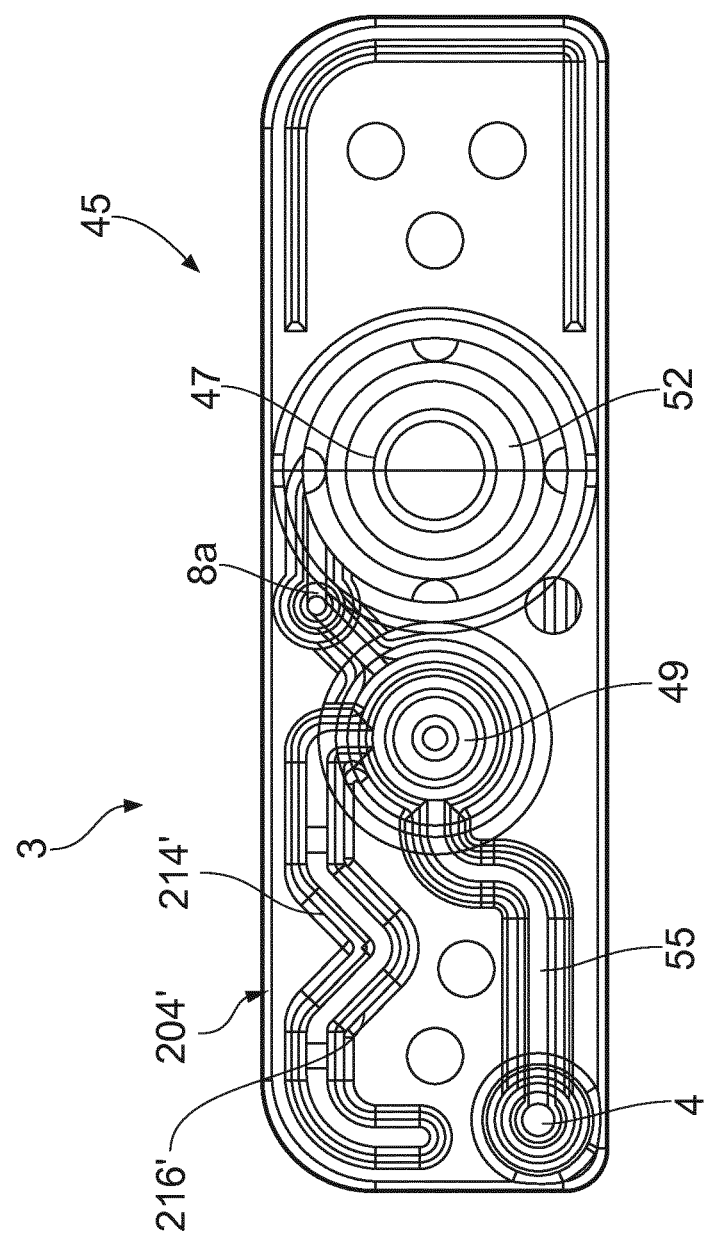
FIG. 6 shows a front view of the cartridge.
Figure 7:
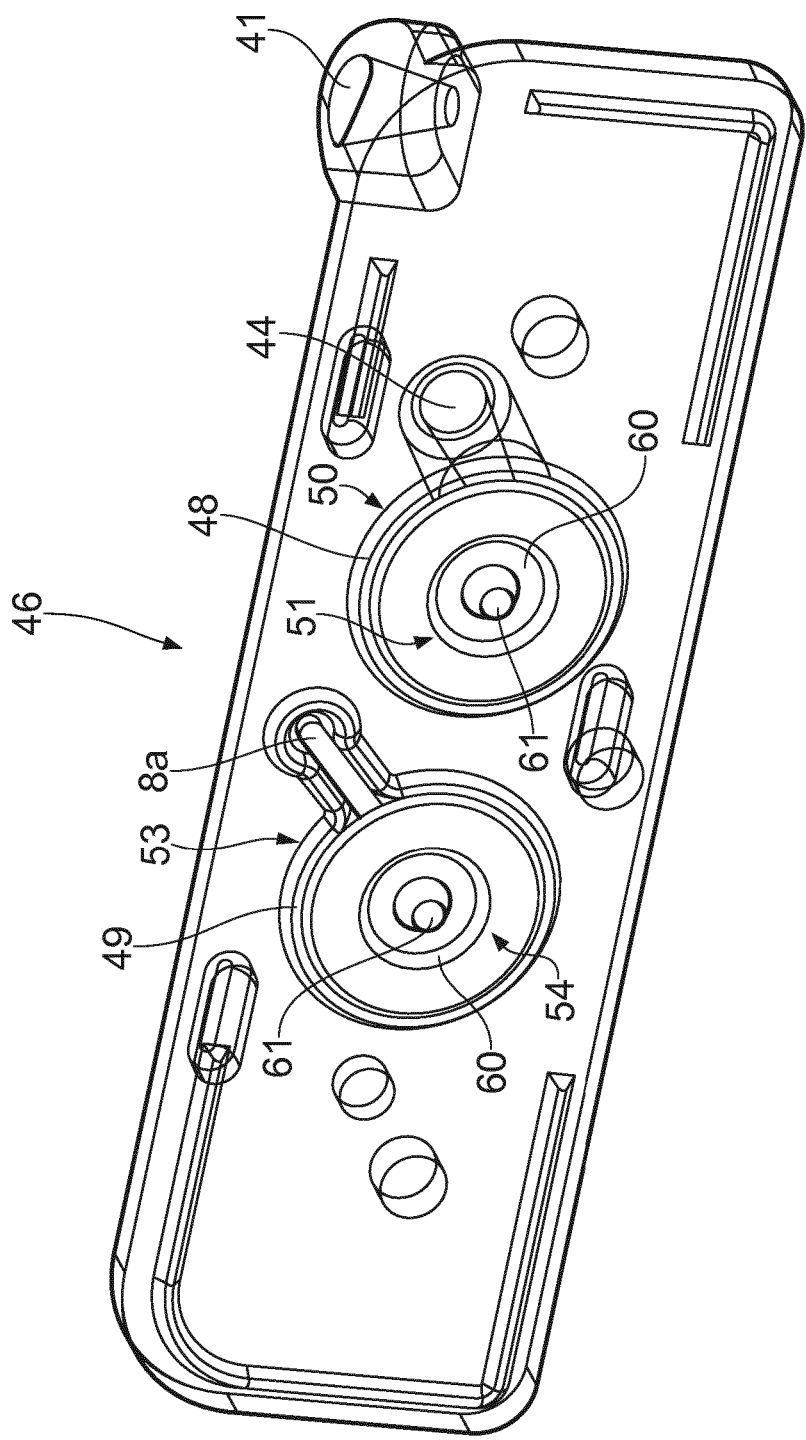
FIG. 7 shows in detail the inlet and outlet valves of the pumping chamber part of the cartridge.

Turning next to FIGS. 5 to 7, the cartridge 3 will now be described in detail. As shown in FIG. 5 the cartridge 3 includes a reservoir case 38 containing the reservoir 7 for storing a supply of insulin. The reservoir 7 is formed as a rectangular frame 39 with front and rear film covers welded onto the frame so as to bound the fluid volume of the reservoir 7. The reservoir 7 fits within the case 38 which provides structural support and protection for the reservoir 7.

At one corner the case 38 includes a filling aperture 41 for receiving a filling needle. Beneath the aperture 41 is a rubberized insert 42 which covers and seals an inlet port 43 of the reservoir 7 passing through the reservoir frame 39. The needle tip penetrates the seal member 42. By connecting a supply of insulin under positive pressure to the filling needle the insulin may be injected through the needle into the inlet port 43 of the reservoir 7 so as to fill the reservoir with insulin. The reservoir frame 39 also includes an outlet port 44 in fluid communication with a pump stack indicated generally by reference number 45.

The pump stack 45 includes a valve assembly 46, the pumping chamber 8 having a pumping chamber membrane 47 and the outlet port 4. FIG. 6 illustrates a front view of the cartridge 3 in detail showing the front face of the pump stack 45, and FIG. 7 illustrates the valve assembly 46 in more detail. The valve assembly 46 includes an inlet valve 48 and an outlet valve 49. The inlet valve 48 has an inlet side 50 fluidically connected via the inlet port 54 to the reservoir 7. Inlet valve 48 also has an outlet side 51 which opens into the pumping chamber 8. The pumping chamber membrane 47 has a front face 52 and a rear face 53, where the rear face 53 forms a boundary to the pumping chamber 8 such that the displacement of the membrane 47 changes a volume of the pumping chamber 8. The pumping chamber membrane 47 sits adjacent the outlet side 51 of the inlet valve 48.

The pumping chamber 8 also comprises a fluid passage 8a extending between the outlet side 51 of the inlet valve 48 and an inlet side 53 of the outlet valve 49. The outlet valve 49 also has an outlet side 54 fluidly connected via conduit 55 to the outlet port 4.

The inlet valve 48 and the outlet valve 49 are each one-way check valves and include an annular elastomeric valve member 60 over a conical valve seat 61 such that the conical valve seat 61 projects through the hole in the centre of the annular valve member 60. The outer periphery of the valve member 60 is fixed—by bonding or clamping, for example—within the pump stack 45. The conical valve seat 61 is projected through the hole in the valve member 60 so that the inner periphery of the elastomeric valve member is deflected by the valve seat 61 and the valve seat 61 forms a seal around the inner periphery of the annular valve member. More particularly, the conical valve seat 61 seals onto an edge of the inner periphery of the hole in the annular valve member.

The sealing is sufficient to prevent flow of fluid from the inlet side to the outlet side of the respective valve unless the pressure on the inlet side is higher that the pressure on the outlet side and the difference exceeds the breakthough pressure of the valve by providing sufficient force to partially and temporarily lift the valve membrane 60 away from the valve seat 61. The force required to lift the valve member 60 away from the valve seat 61 is determined by the extent to which the valve member 60 is deflected by the valve seat 61, the stiffness of the elastomeric valve seat 60 and the surface finish on the valve seat 61. By carefully combining these features, micro valves can be fabricated with different breakthrough pressures.

During filling of the reservoir 7 with fluid, in this case insulin, the fluid is injected under positive pressure sufficient to exceed the breakthrough pressure of the inlet valve 48, which may be set at approximately 100 millibars. In practice, the breakthrough pressure may be in the range of approximately 10 millibars to approximately 500 millibars. This equates to a relatively low tension in the elastomeric valve member 60 of typically less than 1 Newton.

When the pressure in the reservoir 7 during filling exceeds the breakthrough pressure of the inlet valve 48, fluid flows from the reservoir 7 through the reservoir outlet port 44 and into the pumping chamber 8 and starts to build pressure on the inlet side of the outlet valve 49. Once the positive pressure differential between the inlet side and the outlet side of the outlet valve 49 exceeds the breakthrough pressure of the outlet valve 49 the outlet valve 49 opens and fluid passes via conduit 55 to the outlet port 4 of the cartridge 3. With the infusion tube 6 and infusion set 5 connected to the outlet port 4 of the cartridge 3 insulin flows to the infusion set 5 expelling air in the infusion tube 6 and the infusion set 5 until the insulin begins to exit the infusion set 5 indicating that the reservoir 7 is full and the infusion set 5 is primed ready for use.

At this point the injection of insulin through the filling needle into the filling aperture 41 can be stopped, and the pressures in the reservoir 7 will return to ambient causing the inlet valve 48 and the outlet valve 49 to close leaving a positive pressure in the valve apparatus 46. Removal of the filling needle from the filling aperture 41 causes the seal insert 42 to seal the reservoir 7 to prevent escape of insulin from the filling aperture 41. The filled and primed cartridge 3 having the infusion set 5 connected is now ready for coupling to the pump part 2.

The drive member 21 of the actuator 20 rests in a fully extended position such that upon installation of the cartridge 3 in the pump part 2 the aperture membrane 37 stretched over the head 38 of the drive member 21 directly contacts that front face 52 of the pumping chamber membrane 47 so as to deflect the pumping chamber membrane 47 inwardly into the pumping chamber 8 thereby decreasing the volume of the pumping chamber 8. The stretched membrane 37 may achieve a tension of approximately 2 Newtons. In other embodiments the drive member 21 is biased by another component, such as a spring in the actuator 20 or a membrane in the cartridge 3 for example, which may be used in addition to or instead of the biasing function of the membrane 37. Since the pumping chamber 8 is fully filled with insulin (i.e. there are no gas bubbles which may cause a fluid front) the pressure in the pumping chamber temporarily increases at the inlet side 53 of the outlet valve 49 which opens releasing a very small volume of insulin from the outlet valve 49 which exits via the outlet port 4 and from the infusion set 5. This displacement of the pumping chamber 8 is of the order of 10 microlitres or less and preferably is 2.5 microlitres or less.

The drive member 21 of the actuator 20 is controlled to move in reciprocating motion which, by displacement of the pumping chamber membrane 47, causes successive opening and closing of the inlet valve 48.

When the drive member 21 retracts, the pumping chamber membrane 47 partially relaxes out from the pumping chamber which increases the volume of the pumping chamber and thereby decreases the pressure in the pumping chamber 8 such that the positive pressure differential between the inlet side 50 and the outlet side 51 of the inlet valve 48 increases above the breakthrough pressure of the inlet valve so that the inlet valve 48 opens and the pumping chamber 8 fills with insulin from the reservoir 7.

Subsequent extension of the drive member 21 of the actuator 20 stretches the pumping chamber membrane 48 into the pumping chamber which decreases the volume of the pumping chamber 8 and thereby increases the pressure in the pumping chamber 8 until the positive pressure differential between the inlet side 53 and the outlet side 54 of the outlet valve 49 increases above the breakthrough pressure of the outlet valve 49 whereby the outlet valve 49 opens and insulin flows through the outlet valve and via the outlet port 4 to the infusion set 5 for delivery of insulin to the patient.

Using the handset 10 the control electronics in the circuit board 13 of the pump part 2 may be controlled to activate the actuator 20 to provide the required delivery profile of insulin to the patient.

The cartridge 3 may be exchanged for a full cartridge when empty and refilled as described above.

One common problem in infusion systems, and fluid delivery systems more generally, is blockage in the line delivering the fluid from the pump to an outlet. For example, the tube through which fluid is pumped (e.g. the infusion tube 6) may become kinked, or a foreign object may become lodged there. This partial or total blockage is known as a partial or total occlusion, and obviously has an adverse impact on the ability of the system to deliver fluid. It may also have an adverse impact on the mechanics of the system, as repeated attempts to deliver fluid through an occluded tube will generally result in higher pressures on the pump-side of the occlusion.

The fluid delivery system solves this problem by providing an occlusion sensor, which is configured to sense partial or total occlusions within an outlet tube. In response to a total or partial occlusion being sensed, a warning signal can be generated or pumping suspended, for example.

Figure 8:
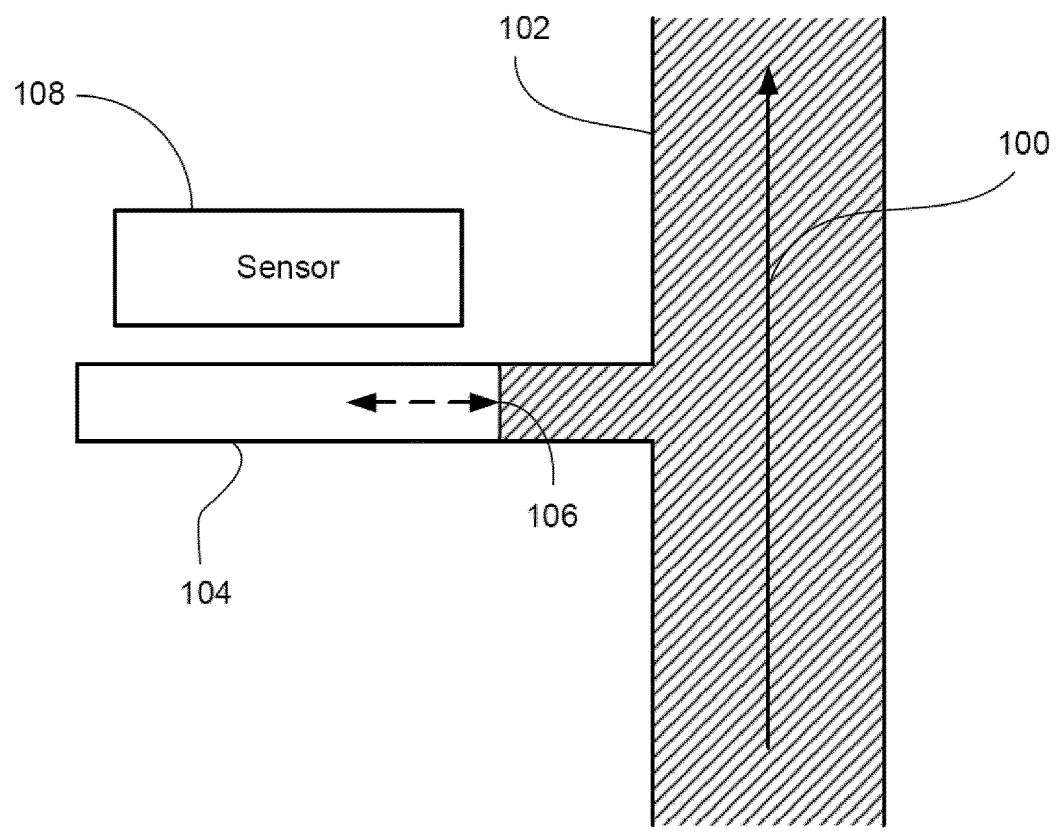
FIG. 8 shows a schematic view of an occlusion-sensing arrangement of the infusion system.

FIG. 8 is a schematic diagram showing the sensing arrangement in its most general form.

A fluid path is shown by arrow 100 along a conduit 102. Liquid is shown by shaded regions. The conduit 102 is connected to a pump (not shown), which acts to drive the liquid under pressure along the fluid path 100. The upper end of the conduit 102 is left open, indicating that the liquid flows along the fluid path towards an outlet.

A sensing tube 104 is in fluid communication with the conduit 102. The sensing tube 104, however, is closed at its distal end. In use, the sensing tube 104 comprises a quantity of gas (e.g. air) which is trapped between its closed distal end, and the presence of liquid at its proximal end. A liquid-gas front 106 thus exists within the sensing tube 104. It should be noted that the sensing tube (or rather its internal bore) has a diameter such that only a single liquid-gas front can exist within the tube. The diameter may be chosen depending upon the liquid which is to be pumped, e.g. one or more of its viscosity, surface tension, etc.

A sensor 108 is provided and configured to detect movement of the liquid-gas front 106 in a manner to be described in greater detail below. In some embodiments, the sensor 108 is provided within a durable part of the fluid delivery system (e.g. the durable pump part 2), while the conduit 102 and the sensing tube 104 are provided in a replaceable part of the fluid delivery system (e.g. the cartridge 3).

Upon activation of the pump, liquid is driven under pressure along the fluid path 100. At the junction with the sensing tube 104, a small amount of liquid will initially enter the sensing tube 104 owing to the lower, atmospheric gas pressure within the tube. However, as the tube 104 is closed, the gas pressure quickly increases as liquid moves into the tube until an equilibrium is reached. At constant liquid pressure, the liquid-gas front 106 thus remains stationary.

Consider the consequences of a partial or total occlusion in the conduit 102, at a location downstream of the sensing tube 104. The occlusion blocks flow of liquid out of the conduit 102, and thus liquid pressure rises as the pump continues to pump fluid into the blocked conduit. This creates a pressure imbalance between the gas and the liquid in the sensing tube 104 (i.e. the equilibrium no longer holds). As liquid pressure is higher, the gas inside the tube 104 is compressed and the front 106 moves further into the tube 104 to maintain the equilibrium.

The sensor 108 is configured to sense movement of the liquid-gas front 106. Upon sensing that movement, the system is able to infer that a partial or total occlusion has occurred within the conduit 102. The sensor 108 may be configured to sense in a discrete fashion whether or not the liquid-gas front 106 has moved, or the degree to which the liquid-gas front 106 has moved.

For example, in the former category, the sensor 108 may be configured to determine at a specific location whether the contents of the sensing tube 104 are liquid or gas, thus inferring movement of the liquid-gas front in the event that the determination changes. The specific location may be chosen so that particular contents are expected at that location under normal operating conditions. For example, the specific location may be chosen to be further towards the closed, distal end of the sensing tube 104 than the location at which the front 106 is expected to be during normal operation (i.e. the equilibrium point under normal pumped liquid pressure). Under normal operating conditions, therefore, the contents of the tube at this location will be a gas. If a liquid is detected at that location, then it can be inferred that the liquid-gas front 106 has moved from its normal location.

Alternatively, the sensor 108 may be configured to sense the presence or absence of the liquid-gas front 106 itself at a specific location, thus inferring movement of the liquid-gas front. For example, the sensor 108 may be configured to detect the presence or absence of a front at a single location along the sensing tube at which the front 106 is expected to be during normal operation (i.e. the equilibrium point under normal pumped liquid pressure). If the front 106 is at that location, then it can be inferred that the system is operating normally. If the front 106 is absent from that location, then movement of the front can be inferred. Similarly, the sensor 108 may be configured to detect the presence or absence of a front at a single location which is further along the sensing tube 104 than where it is expected to be during normal operation (e.g. closer to the sensing tube's distal end than the equilibrium point under normal pumped liquid pressure). If a front is detected at that location, then it can be inferred that the front has moved from its normal location. These mechanisms can be used to provide a discrete output of whether or not movement of the liquid-gas front has been sensed and thus whether or not an occlusion has occurred downstream in the conduit 102.

Alternatively, the sensor 108 may be configured to sense a degree of movement of the front 106. For example, the sensor may be configured to detect the contents of the sensing tube 104 at multiple discrete locations along the length of the sensing tube 104 (i.e. whether the contents are liquid or gas). From this, the location of the liquid-gas front 106 can be determined and tracked as it moves. Alternatively, the sensor 108 may be configured to sense the presence or absence of the liquid-gas front 106 at multiple discrete locations along the sensing tube 104. Again, the location of the front 106 can therefore be tracked over time and the degree of movement sensed. In yet further embodiments, the sensor 108 may be configured to sense one or more properties of the sensing tube 104 and its contents over a length of the sensing tube (i.e. along either its whole length or part of its length), and infer movement of the liquid-gas front from changes in the values of those properties. The sensor may further measure the time frame over which the movement occurs.

The sensor 108 may provide a discrete output indicating whether or not an occlusion has occurred, or a range of outputs indicating the likelihood that an occlusion has occurred, or the degree of the occlusion which has occurred (i.e. whether the occlusion is total or partial). In the former category, the sensor 108 may utilise any of the mechanisms which detect whether the front 106 has moved or not (i.e. the discrete mechanisms) to infer directly whether or not an occlusion has occurred. Alternatively, the sensor 108 may utilise any of the mechanisms which sense the degree of movement of the front 106, and then compare that degree of movement to a threshold value to provide a discrete output of whether or not an occlusion has occurred. If the degree of movement exceeds the threshold, an occlusion can be inferred. If the degree of movement does not exceed the threshold, an occlusion may not be inferred.

The sensor 108 may utilize any of the mechanisms which sense the degree of movement of the front 106 to infer whether or not an occlusion has occurred and/or the degree of occlusion which has occurred (i.e. whether the occlusion is total or partial). For example, relatively large movement of the front 106 may be indicative of a significant or total occlusion. Relatively little movement of the front 106 may be indicative of a less significant or partial occlusion.

If the time over which movement of the front occurs is also measured, this data may additionally be used to infer whether or not an occlusion has occurred and/or the degree of the occlusion which has occurred. For example, a front 106 which moves relatively rapidly along the sensing tube 104 may be indicative of a significant, or total occlusion. A front 106 which moves less quickly along the sensing tube 104 may be indicative of a less significant or partial occlusion.

Once it has been determined that an occlusion has occurred, the system may react in a number of ways. In one embodiment the sensor may cause to be generated a control signal instructing the pump to cease or suspend pumping. In the system described above, for example, the durable pump part 2 may cease or suspend further operation of the actuator 20. Alternatively, or additionally, the sensor may cause to be generated a user output, informing the user of the detected occlusion. In the system described above, for example, the durable pump part 2 may transmit a signal to the handset 10, informing the handset of the occlusion; the handset 10 can then respond by displaying a warning message to the user via the interface 11.

Various mechanisms can be provided to sense movement of the liquid-gas front 106, and a number of different embodiments will be discussed below.

Figure 9A:
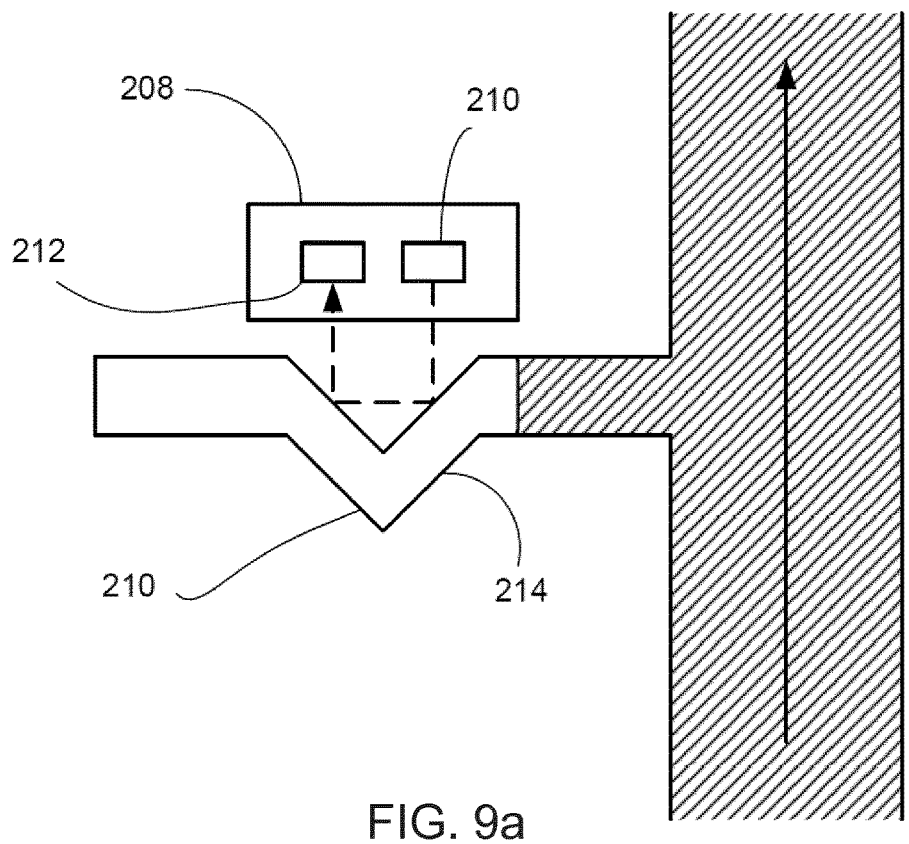
FIG. 9a shows a schematic view of an occlusion-sensing arrangement comprising an optical sensor.

FIG. 9a is a schematic illustration of one mechanism for detecting movement of the liquid-gas front 106 within the sensing tube 104.

In this embodiment, the sensor 208 is provided with an optical transmitter 210 for transmitting optical light primarily in a direction towards the sensing tube 204, and an optical detector 212 for detecting optical light which is reflected off the sensing tube 204. The optical transmitter 210 may be an LED, for example, while the optical detector 212 may be a photodiode, for example. The optical light may have a wavelength in the infrared portion of the electromagnetic spectrum.

In the illustrated embodiment, the sensing tube comprises a first part 214 which is obliquely angled with respect to the transmitted light, such that the light is reflected off the first part at an angle away from the optical transmitter 210. In the illustrated embodiment, the first part is oriented at an angle of approximately 45° with respect to the transmitted light. The sensing tube 204 further comprises a second part 216 which is positioned with respect to the first part 214 such that the light which is reflected off the first part is primarily reflected towards the second part 216. The second part 216 is angled with respect to the first part 214 such that the reflected light is further reflected in a direction which is anti-parallel to the direction of the light as it leaves the optical transmitter 210. In this way, a significant portion of the light which is transmitted from the optical transmitter 210 is reflected back towards the optical detector 212.

The refractive index of the tube 204 changes as its contents change. For example, if the tube is full of liquid at a location where optical light is incident, the angle at which the light is reflected and/or the amount of light which is reflected will be different than if the tube is full of gas at that location, or if the liquid-gas front 106 itself is present at that location. Thus, as the liquid-gas front 106 moves along the sensing tube 204 (e.g. due to an occlusion in the conduit 102), the presence of liquid in the first part 214 and potentially the second part 216 will affect the amount of light which reaches the detector 212. For example, in one embodiment, the sensing tube 204 is arranged such that the magnitude of the light signal detected at the detector 212 is a first value when the first part 214 and the second part 216 have gas in them; a second, different value when the first part 214 has liquid in it and the second part 216 has gas in it; and a third value when the first part 214 and the second part 216 have liquid in them. The third value is different from at least the second value, and may also be different to the first value. Thus, the location of the liquid-gas front 106 may be tracked by detecting the light which is reflected off the sensing tube 204.

In an embodiment, the sensor 208 may be calibrated to match a detected magnitude of the light signal detected at the detector 212, to a corresponding location of the liquid-gas front 106. A look-up table may be provided so that the location of the liquid-gas front 106 can be easily determined based on a given signal detected at the detector 212. In other embodiments, the sensor 208 may be arranged to infer that the front 106 has moved on the basis of a changed signal at the detector 212.

In the illustrated embodiment, the sensing tube 204 has two angled parts 214, 216. This provides information on two locations of the sensing tube 204. However, it will be apparent to the skilled person that more than two angled parts, or a single angled part, may be provided, in order to angle transmitted optical light off the sensing tube towards the location of an optical detector. The sensing tube 204 may not have any angled parts, provided that the detector 212 is able to detect light which is transmitted towards, and reflected off the sensing tube 204.

It will be apparent now that the embodiment schematically shown in FIG. 9a is also shown in the embodiments described above and shown in more detail in FIGS. 3 and 6. FIG. 3 shows the durable pump part 2, and particularly the recess 18 which is shaped to accept a similarly shaped cartridge 3. Two ports 71, 72 are shown in a wall of the recess 18. One port 72 corresponds to the location of the optical transmitter 210, while the other port 71 corresponds to the location of the optical detector 212. The durable pump part 2 thus comprises the sensor 208, located behind the two ports 71, 72.

FIG. 6 shows the outlet valve 49 having an outlet side 54 fluidly connected via conduit 55 to the outlet port 4. Also fluidly connected to the outlet side 54 of the outlet valve 49 is a closed sensing tube 204'. As the sensing tube 204' is fluidly connected to the outlet side 54 of the outlet valve 49, together with the conduit 55, the outlet port 4 and, ultimately, the infusion tube 6, changes in pressure resulting from occlusions within any of those parts can be detected by the sensing tube 204' in the manner described above.

The sensing tube 204' has two angled parts 214', 216' and these are positioned within the cartridge 3 such that they are aligned with respect to ports 71, 72 in the manner shown schematically in FIG. 9a when the cartridge 3 is inserted within the recess 18. The cartridge 3 also has a window, which is substantially transparent to optical light, in the vicinity of the sensing tube 204' such that optical light transmitted by the transmitter 210 reaches the sensing tube 204', while optical light reflected off the sensing tube 204' reaches the detector 212. In this way, the electrical parts (i.e. sensor 208) are kept within the durable pump part 2, while the mechanical parts (i.e. the sensing tube 204') are kept within the removable cartridge. This arrangement therefore requires no additional connections between the sensor 208 and the sensing tube 204' for the sensor to be made operational; the sensor is connected to the sensing tube simply by inserting the cartridge 3 into the recess 18.

Figure 9B:
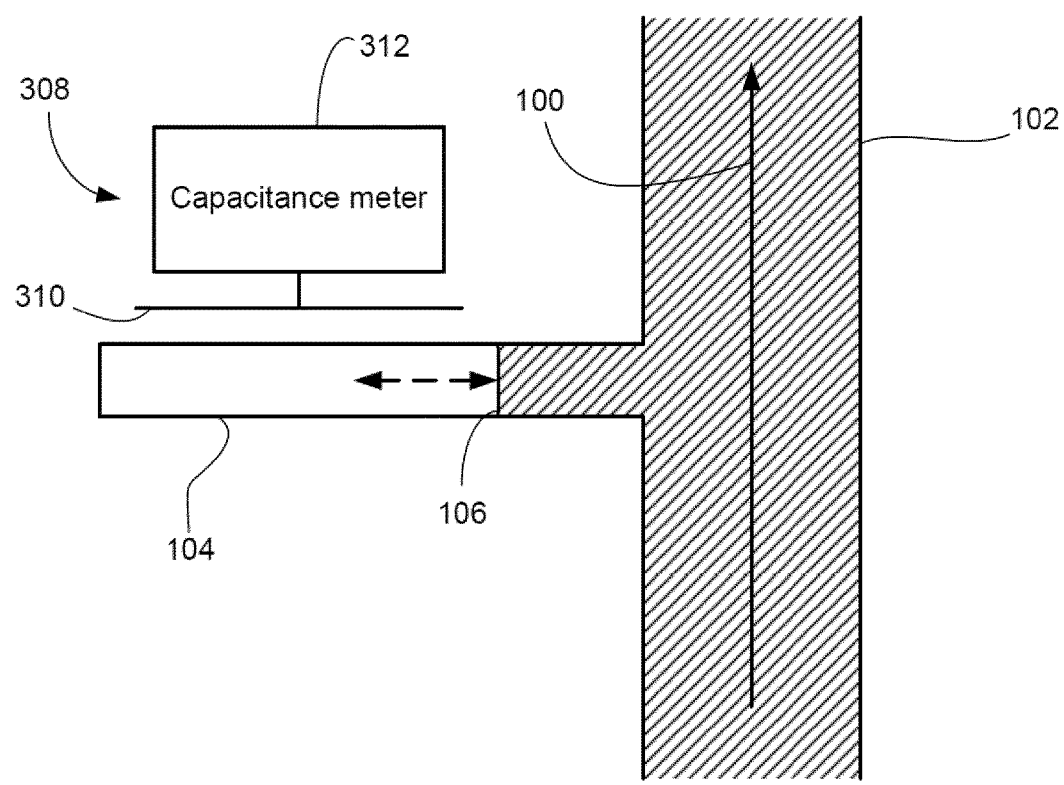
FIG. 9b shows a schematic view of an occlusion-sensing arrangement comprising a sensor for measuring capacitance.

FIG. 9b shows in schematic form an alternative mechanism for sensing movement of a liquid-gas front 106 within the sensing tube.

In this arrangement, the sensor 308 comprises a capacitive plate 310 positioned adjacent to the sensing tube 104, and a capacitance meter 312 operatively coupled to the capacitive plate 310.

As will be understood by those skilled in the art, the capacitance of the capacitive plate 310 will change as liquid moves along the sensing tube 104 (i.e. displacing the gas) in proximity to the capacitive plate 310, owing to the different permittivities of liquid and gas. Such changes can be measured by the capacitance meter 312, and used to infer movement of the liquid-gas front 106 within the sensing tube 104.

The sensor 308 is thus able to detect changes in the contents of the tube 104 at locations in proximity to the capacitive plate 310. In the illustrated embodiment, the capacitive plate 310 extends along a substantial part (e.g. a majority) of the length of the sensing tube 104 and, in this arrangement, the sensor 308 may be able to detect movement of the front 106 along at least that same substantial part of the tube. The sensor 308 may thus be able to detect a degree of movement of the front 106.

In an embodiment, the sensor 308 may be calibrated to match a detected capacitance to a corresponding location of the liquid-gas front 106. For example, a look-up table may be provided so that the location of the liquid-gas front 106 can be easily determined based on a given capacitance.

In other embodiments, one or more capacitive plates may be provided in proximity to the sensing tube 104 at respective locations along the length of the tube 104. By sensing changes in capacitance at each capacitive plate, the location of the front 106, or merely that the front 106 has moved, can be readily inferred.

Figure 9C:
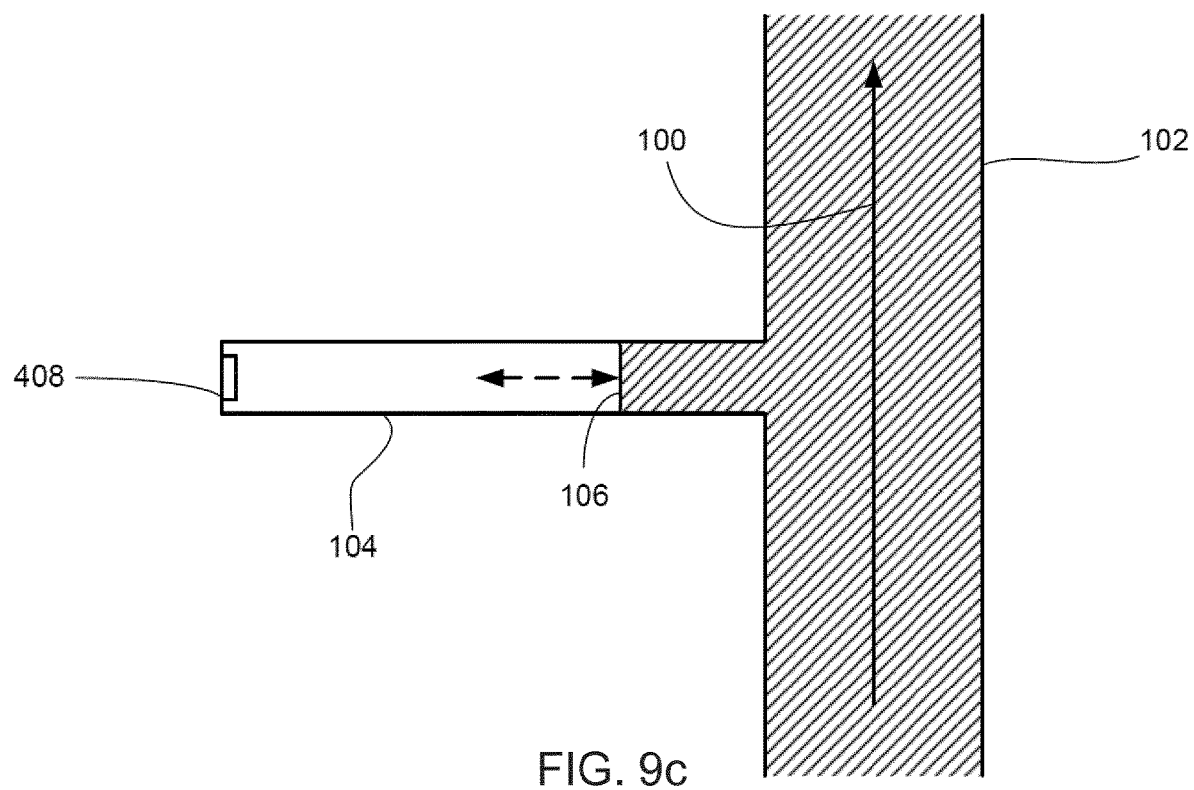
FIG. 9c shows a schematic view of an occlusion-sensing arrangement comprising a pressure sensor.

FIG. 9c shows in schematic form a further alternative mechanism for sensing movement of a liquid-gas front 106 within the sensing tube.

In this arrangement, the sensor 408 comprises a pressure sensor arranged to detect the gas pressure within the sensing tube. In the illustrated embodiment, the pressure sensor is formed inside the sensing tube 104, at the closed, distal end thereof, ensuring that the sensor detects only gas pressure (and does not come into contact with liquid).

When an occlusion occurs, the liquid pressure rises as the pump continues to pump water along the blocked fluid path. As discussed above, this causes the liquid-gas front 106 to move along the sensing tube 104. Of course, the gas pressure will also increase as the gas is compressed within the tube by the moving front 106.

This sensor arrangement is therefore able to report in a number of ways: sensing any change in the gas pressure (relative to normal operating conditions), and inferring that an occlusion has occurred; sensing a change in pressure (relative to normal operating conditions) that is greater than a threshold, and inferring that an occlusion has occurred; sensing the change in pressure and inferring the degree of occlusion that has occurred.

In its simplest form, the sensor 408 can be a pressure switch, designed to actuate once a particular pressure is reached. The particular pressure can be predetermined to be a pressure which is indicative of an occlusion.

Figure 9D:
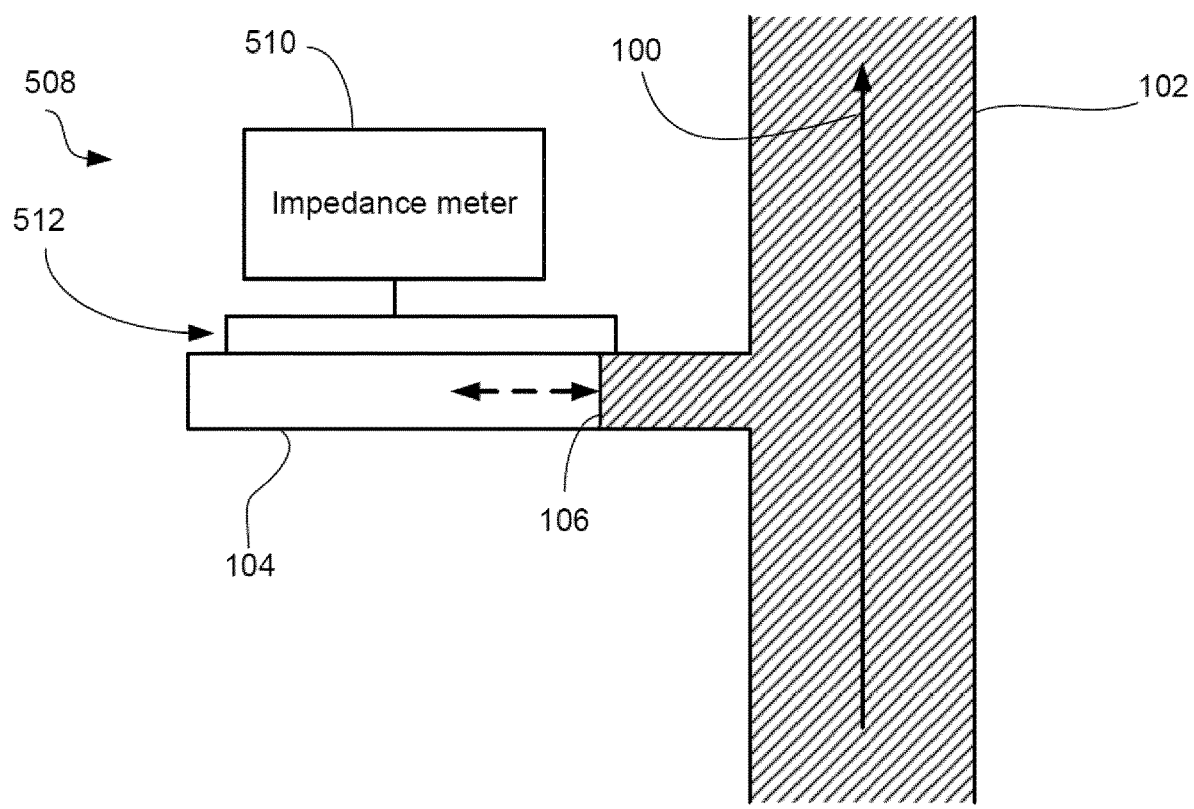
FIG. 9d shows a schematic view of an occlusion-sensing arrangement comprising a sensor for measuring impedance.

FIG. 9d shows in schematic form a yet further alternative mechanism for sensing movement of a liquid-gas front 106 within the sensing tube.

In this arrangement, the sensor 508 comprises an impedance meter 510 having a plurality of electrical terminals 512 arranged along the length of the sensing tube 104. The impedance meter 510 is configured to measure the impedance between any two of the terminals 512, and so infer the position of the liquid front 106. The inference can be made as impedance will drop significantly if the two terminals are connected together via liquid.

In one embodiment, the sensor 508 comprises two electrical terminals: a first terminal at a location where liquid is expected to occupy the tube 104 during normal operating conditions (i.e. without an occlusion); and a second terminal at a location where gas is expected to occupy the tube 104 during normal operating conditions. The second terminal may be provided at a location where the presence of the liquid front 106 (i.e. once it has moved) is indicative of an occlusion. For example, the second terminal may be provided at a location which is adjacent to the position of the front 106 under normal operating conditions (such that any movement of the front 106 along the tube connects the two terminals), or a threshold distance away from that position to prevent only minor changes in pressure resulting in (false) detection of occlusions.

In other embodiments, the sensor 508 comprises more than two electrical terminals arranged along the length of the tube 104, such that the position of the front 106 can be inferred more accurately. The terminals may be regularly spaced along the length of the tube 104, for example.

The embodiments described above have the advantage that no special steps are required to prime the occlusion-sensing mechanism for operation, or to reset the mechanism after an occlusion has been detected. The arrangement includes a closed sensing tube, coupled to a fluid path along which liquid is pumped. Prior to pumping, the sensing tube simply contains a gas such as air. During pumping, occlusions can be detected or inferred by movement of a liquid-gas front along the sensing tube. Once the occlusion has been detected (and cleared), the liquid which has entered the sensing tube is automatically expelled under the pressure of the compressed gas. No special steps are required to reset the mechanism for further operation.

Those skilled in the art will appreciate that various amendments and alterations can be made to the embodiments described above without departing from the scope of the invention as defined in the claims appended hereto.

The invention claimed is:

1. A fluid delivery system, comprising:
an outlet tube;
a pump for pumping liquid along a fluid path including the outlet tube;
a replaceable cartridge;
a closed sensing tube branched from the fluid path which, in use, is filled with gas; and
a sensor configured to sense whether the contents within the sensing tube are a liquid or gas to determine movement of a liquid front within the sensing tube and, responsive to sensing of said movement, determine that a partial or total occlusion has occurred within the outlet tube, the sensor configured to sense (1) the refractive index of the sensing tube which changes with the contents of the sensing tube, (2) the permittivities of the contents of the sensing tube, or (3) the impedance of the contents of the sensing tube,
wherein the replaceable cartridge comprises a reservoir and the closed sensing tube, and
wherein the pump is configured to pump liquid from the reservoir along the fluid path.

2. The fluid delivery system according to claim 1, wherein a bore of the sensing tube has a diameter such that only a single liquid front can exist within the sensing tube.

3. The fluid delivery system according to claim 2, wherein the diameter of the bore of the sensing tube is sized to maintain the single liquid front in any orientation of the sensing tube.

4. The fluid delivery system according to claim 1, wherein the replaceable cartridge comprises an optically transparent window allowing viewing of the sensing tube.

5. The fluid delivery system according to claim 1, wherein the sensor is located outside the replaceable cartridge.

6. The fluid delivery system according to claim 1, wherein the sensor is configured to transmit optical light towards the sensing tube, and to detect light which is scattered off the sensing tube.

7. The fluid delivery system according to claim 6, wherein the sensor comprises a transmitter for transmitting optical light towards the sensing tube, and a detector for detecting the scattered light which is scattered off the sensing tube.

8. The fluid delivery system according to claim 7, wherein the transmitter and the detector are located at different locations, and wherein the transmitter is arranged to transmit optical light towards a portion of the sensing tube which is obliquely angled with respect to the transmitted optical light, such that the optical light is primarily scattered directly or indirectly towards the detector.

9. The fluid delivery system according to claim 7, wherein the transmitter is an LED.

10. The fluid delivery system according to claim 6, wherein the sensor is configured to sense movement of the liquid front within the sensing tube by detecting a change in the detected scattered light.

11. The fluid delivery system according to claim 6, wherein the optical light is infrared.

12. The fluid delivery system according to claim 1, wherein the sensor comprises one or more capacitive plates positioned adjacent to the sensing tube, and wherein the sensor is configured to sense movement of the liquid front within the sensing tube by detecting a change in the capacitance of said one or more capacitive plates.

13. The fluid delivery system according to claim 1, wherein the sensor comprises an impedance sensor configured to sense movement of the liquid front within the sensing tube by detecting a change in the impedance of the sensing tube.

14. The fluid delivery system according to claim 1, wherein the fluid path begins at an outlet valve of the pump.

15. The fluid delivery system according to claim 1, wherein the sensing tube is stationary with respect to the sensor and the sensor is configured to sense the movement of the liquid front within the stationary sensing tube.

16. The fluid delivery system according to claim 1, wherein the sensor is configured to sense whether the contents within a sensing region of the sensing tube are a liquid or gas to determine the movement of the liquid front within the sensing tube.

17. The fluid delivery system according to claim 1, wherein the replaceable cartridge further comprises a pumping chamber, and wherein the pump is for pumping liquid from the reservoir to the pumping chamber along the fluid path.

18. The fluid delivery system according to claim 1, wherein the system further comprises a housing, wherein the housing comprises the pump, and the replaceable cartridge can be removably attached to the housing.

* * * * *